US007648761B2

(12) United States Patent
Bayram-Hahn et al.

(10) Patent No.: US 7,648,761 B2

(45) Date of Patent: Jan. 19, 2010

(54) INORGANIC MONOLITHIC MOULDINGS COATED WITH ORGANIC POLYMERS

(75) Inventors: Zöfre Bayram-Hahn, Mainz-Kostheim (DE); Klaus Unger, Seeheim-Jugenheim (DE); Robertus Hendriks, Heidelberg (DE); Dieter Lubda, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 18 days.

(21) Appl. No.: 10/532,877

(22) PCT Filed: Oct. 21, 2003

(86) PCT No.: PCT/EP03/11612

§ 371 (c)(1), (2), (4) Date: Apr. 28, 2005

(87) PCT Pub. No.: WO2004/039495

PCT Pub. Date: May 13, 2004

(65) Prior Publication Data

US 2006/0099402 A1 May 11, 2006

(30) Foreign Application Priority Data

Oct. 31, 2002 (EP) ................................ 02024250
Oct. 31, 2002 (EP) ................................ 02024251

(51) Int. Cl.
*B32B 3/26* (2006.01)
*C08F 2/46* (2006.01)

(52) U.S. Cl. .............. 428/319.3; 428/312.2; 428/312.6; 428/315.7; 428/319.7; 427/487; 427/498; 427/301; 427/327

(58) Field of Classification Search .............. 428/312.2, 428/312.6, 319.3, 319.7, 315.7
See application file for complete search history.

(56) References Cited

U.S. PATENT DOCUMENTS

| | | | |
|---|---|---|---|
| 4,308,254 A | 12/1981 | Tayot et al. | |
| 4,483,940 A * | 11/1984 | Ono et al. | 502/159 |
| 4,851,163 A * | 7/1989 | Stanton et al. | 261/122.1 |
| 5,271,833 A | 12/1993 | Funkenbusch et al. | |
| 5,897,915 A | 4/1999 | St. Julien et al. | |
| 6,054,052 A * | 4/2000 | Dhingra et al. | 210/656 |
| 6,398,962 B1 | 6/2002 | Cabrera et al. | |
| 6,863,820 B2 * | 3/2005 | Cabrera et al. | 210/635 |
| 7,125,488 B2 * | 10/2006 | Li | 210/198.2 |
| 7,250,214 B2 * | 7/2007 | Walter et al. | 428/405 |
| 2002/0041041 A1 * | 4/2002 | Johnson | 261/122.1 |
| 2003/0172674 A1 * | 9/2003 | Lubda et al. | 65/17.2 |

FOREIGN PATENT DOCUMENTS

| | | |
|---|---|---|
| DE | 199 29 073 | 1/2001 |
| DE | 10030665 A1 * | 1/2002 |
| EP | 0 838 257 | 4/1998 |
| WO | WO 94/19687 | 9/1994 |
| WO | WO 95/03256 | 2/1995 |
| WO | WO 98/29350 | 7/1998 |

* cited by examiner

*Primary Examiner*—Hai Vo
(74) *Attorney, Agent, or Firm*—Millen, White, Zelano, Branigan, P.C.

(57) ABSTRACT

The present invention relates to inorganic monolithic mouldings whose surface is coated with physi- or chemisorbed organic polymers, and to processes for the production of materials of this type. The materials according to the invention are highly suitable as sorbents for chromatography, in particular for high pressure liquid chromatography of biological materials.

23 Claims, 2 Drawing Sheets

A

B

INORGANIC MONOLITHIC MOULDINGS COATED WITH ORGANIC POLYMERS

The present invention relates to inorganic monolithic mouldings whose surface is coated with physi- or chemisorbed organic polymers, and to processes for the production of materials of this type. The materials according to the invention are highly suitable as sorbents for chromatography, in particular for high pressure liquid chromatography of biological materials.

Chromatographic support materials or sorbents, which are employed for the separation or purification of biological materials, such as proteins, nucleic acids, etc., have to have high alkali stability besides good separation properties. The reason for this are, in particular, special cleaning and sterilisation processes to which the sorbents are subjected.

For example, in the so-called clean in place process, the sorbent is treated with 1M sodium hydroxide solution over a period of 10 minutes to three hours, depending on the column dimension. In order to prevent microbial contamination, the support materials are stored in 0.1M sodium hydroxide solution for long-term storage. Not all support materials are stable under such conditions. For example, inorganic support materials based on silicon dioxide are often not sufficiently stable under the said conditions.

For this reason, organic polymers, such as dextran, agarose, cellulose, polystyrene or methacrylate esters, or inorganic particulate materials coated with such organic polymers are frequently employed as support materials in biochromatography.

Examples of polymer-coated inorganic particles are given, for example, in U.S. Pat. No. 4,308,254 or U.S. Pat. No. 5,271,833. U.S. Pat. No. 4,308,254 discloses inorganic porous particles, for example made from silica, aluminium oxide, magnesium oxide or titanium oxide, which are coated with polysaccharide polymer. U.S. Pat. No. 5,271,833 discloses inorganic oxide particles which are surrounded by an organic polymer.

The disadvantage of the purely organic polymers is a frequently unfavourable pore structure and, as a consequence, an inadequate specific surface area. In addition, polymers with a low degree of crosslinking, in particular, swell considerably in certain solvents.

In polymer-coated particles, these disadvantages can only be overcome to a certain degree by the stable inorganic core. In particular, fairly small particles usually have to be employed in order to ensure a sufficiently high separation efficiency, which results in a considerable increase in the column back pressure. In particular at high pressure, the particles cluster together relatively closely. The flexible polymer layer is considerably deformed in the process, in particular by the inflexible inorganic core, and in some cases even destroyed. This also naturally results in a considerable impairment of the separation efficiency and the service lives of the column.

A further approach is disclosed in DE 199 29 073. Here, the pores of a porous inorganic rod are completely filled with a polymer phase comprising spherical particles connected to one another. Although mouldings whose pores are completely filled with polymer are relatively easy to produce, they exhibit, however, only moderate suitability for chromatographic applications due to the pores completely filled with polymer spheres. On the one hand, the polymer spheres in the channels of the monolith naturally have the same properties as polymer spheres which are packed directly into a column, and thus also have the same disadvantages. On the other hand, there is a considerable danger that relatively small channels in particular are completely blocked and thus inhomogeneous pressure conditions arise in the monolith, again resulting in an impairment of the separation properties.

It has now been found that the above-mentioned disadvantages can be overcome by the use of polymer-coated inorganic monolithic mouldings. To this end, the inorganic porous monolithic mouldings are uniformly covered with a coating of organic polymer. The pre-defined rigid structure of the monolithic material prevents deformation or destruction of the sorbent, even at high pressure. In addition, a suitable choice of the pore structure of the inorganic moulding and of the coating method allows the production of sorbents which exhibit only a moderate column back pressure, even at high flow rates.

Figure 1:
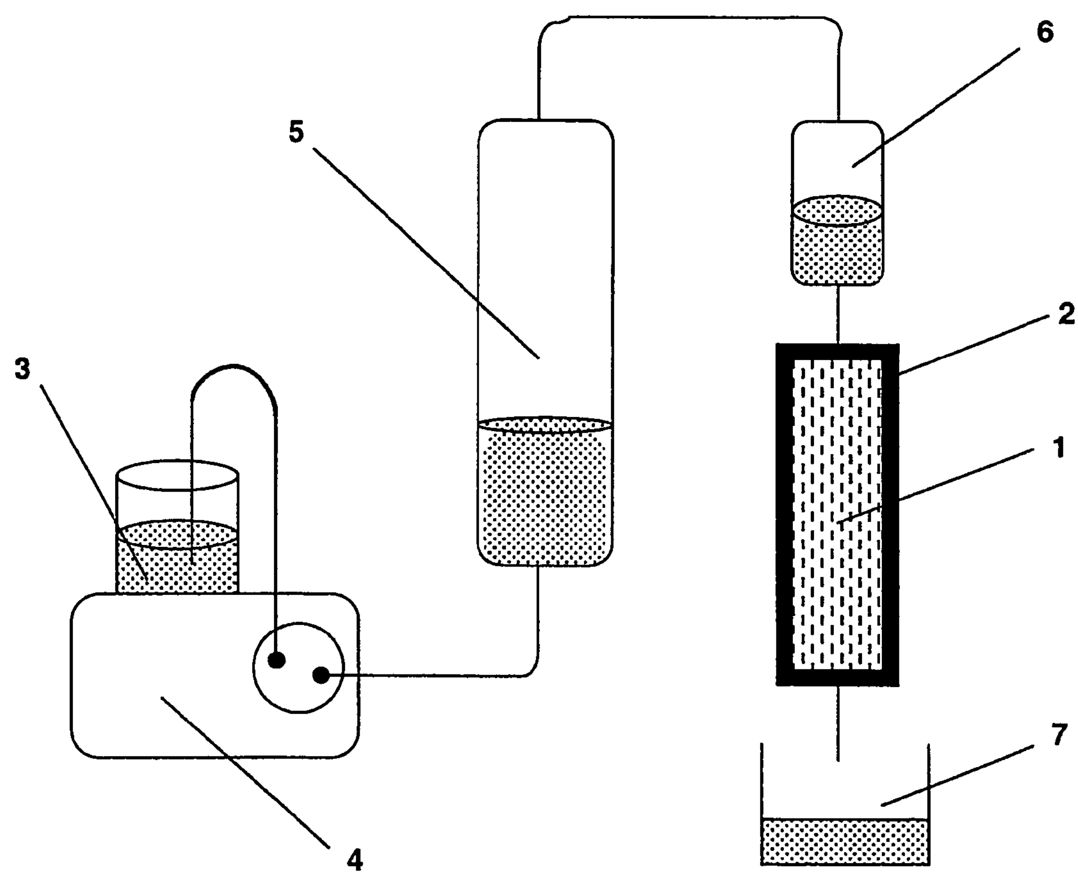
FIG. 1 depicts an appartus for coating foreign bodies by precipitation of prepolymers.

The present invention therefore relates to porous inorganic monolithic mouldings which are coated with at least one organic polymer.

In a preferred embodiment, the porous inorganic monolithic mouldings are materials based on $SiO_2$.

In a particularly preferred embodiment, the porous inorganic monolithic mouldings have a bimodal pore structure with mesopores having a diameter of between 2 and 100 nm and macropores having a mean diameter of greater than 0.1 μm.

In a further preferred embodiment, the organic polymers are polystyrenes or poly(meth)acrylates, and other poly(meth)acrylic acid derivatives, such as, for example, poly(meth)acrylamide derivatives.

In a preferred embodiment, the organic polymer is physisorbed on the inorganic moulding.

The present invention furthermore relates to a process for the production of porous inorganic monolithic mouldings which are coated with at least one organic polymer, which has the following process steps:

a) provision of a porous inorganic monolithic moulding
b) impregnation of the porous inorganic monolithic material from step a) with a coating solution comprising at least organic prepolymers or mono- and/or oligomers.
c) coating of the moulding, where the moulding, during the coating, is clad in an impermeable manner, at least on the long sides, with an inert material or stored in an inert solvent
d) washing and drying of the moulding from step c) for the removal of reaction residues and solvent In a preferred embodiment, in step c) the prepolymers or monomers and/or oligomers are precipitated from the coating solution onto the inorganic moulding.

In a particularly preferred embodiment, the precipitation is carried out by lowering the temperature.

The present invention also relates to the use of the mouldings according to the invention for the chromatographic separation of at least two substances, in particular for the separation and/or purification of biological materials.

For the purposes of the present invention, mouldings are, in particular, mouldings which can be employed as a single piece for chromatographic separations and are not, like particles, introduced in large number into a column. In particular, these are flat or columnar mouldings. Flat mouldings have their greatest dimension perpendicular to the through-flow direction of the eluent. Particular preference is given to columnar mouldings, which have an equally long or longer dimension along the axis through which the eluents flow. The size and dimension of the mouldings corresponds to the usual dimensions for use in chromatography. Flat mouldings typically have a thickness of between 0.2 and 20 μm, columnar mouldings typically have a diameter of between 0.1 cm and 5 cm and a length (longest dimension) of between 1 and 30 cm. For preparative separations, the stated dimensions can be exceeded corresponding to the dimensions of known column dimensions. For miniaturised applications, the stated dimensions can be reduced down to the region of capillaries.

The porous inorganic monolithic mouldings typically consist of inorganic oxides, such as aluminium oxide, titanium dioxide or preferably silicon dioxide.

Of major importance for the suitability of the coated mouldings according to the invention as chromatographic sorbents is the pore structure of the inorganic mouldings. On the one hand, it influences how homogeneously the polymer coating can be applied to the moulding. On the other hand, it influences the separation efficiency and the column back pressure of the coated mouldings. Mouldings which are suitable in accordance with the invention have at least pores which still facilitate flow through the moulding, even after the coating. Preference is therefore given to materials which have at least macropores.

Materials having a bimodal pore distribution, i.e. mouldings which have both macro- and also mesopores, have proven particularly advantageous. The additional mesopores enable a greater surface area to be provided at a low liquid counterpressure.

Particular preference is therefore given in accordance with the invention to the use of inorganic porous monolithic mouldings which have macropores having a mean diameter of greater than 0.1 μm and mesopores in the walls of the macropores, where the mesopores have a diameter of between 2 and 100 nm. Materials of this type can be produced, for example, by a sol-gel process corresponding to WO 95/03256 and particularly preferably corresponding to WO 98/29350.

Organic polymers which are suitable for coating the mouldings are organic materials which can be applied to the moulding as oligomer and/or polymer or organic oligomers and/or monomers which are applied to the moulding by polymerisation or polycondensation. The organic polymers can be chemi- or physisorbed on the moulding.

Suitable organic polymers are, for example, polystyrenes, polymethacrylates, melamines, polysaccharides, polysiloxanes and derivatives thereof or copolymers of two or more suitable compounds, such as, for example, a coating of tetraalkoxysilane and methyltrialkoxysilane. Also suitable are copolymers of the above-mentioned substances with monomers which already carry separation effectors which are suitable for chromatography, such as, for example, copolymers of polystyrenes with compounds carrying ion exchanger groups. Preference is given to chemi- or physisorbed polystyrenes or polystyrene derivatives, particular preference is given to physisorbed poly(meth)acrylates or poly(meth)acrylate derivatives, and other poly(meth)acrylic acid derivatives, such as, for example, poly(meth)acrylamide derivatives. These include, in particular, poly(methacrylate), poly(2-hydroxyethyl methacrylate), a copolymer of 2-hydroxyethyl methacrylate and ethyl methacrylate or poly(octadecyl methacrylate). The polymer coating can take place in accordance with the invention in various ways:

1) by polymerisation or polycondensation of physisorbed monomers and/or oligomers without formation of covalent bonds to the inorganic moulding
2) by polymerisation or polycondensation of physisorbed monomers and/or oligomers with formation of covalent bonds to the inorganic moulding
3) by immobilisation (physisorption) of prepolymers without formation of bonds to the inorganic moulding
4) by chemisorption of prepolymers on the inorganic mouldings.

A solution which is employed for the coating according to the invention of the mouldings accordingly comprises either organic prepolymers or monomers and/or oligomers. In addition, it typically comprises a suitable solvent and optional further constituents, such as, for example, free-radical initiators. It is referred to in accordance with the invention as coating solution.

Prepolymers here means that use is made of already oligomerised and/or polymerised compounds which, after introduction into the moulding, are not subjected to any further polymerisation reaction, i.e. are not cross-linked further with one another. Depending on the nature of the application, they are adsorbed onto the moulding (physisorption) or covalently bonded to the moulding (chemisorption).

By contrast, monomers and/or oligomers are compounds which are suitable for polymerisation or polycondensation and which are crosslinked or polymerised further by polymerisation of polycondensation after introduction into the moulding. Oligomers here are compounds which have already been generated in advance by crosslinking or polymerisation of monomers.

It has been found that processes for the coating of particles can only be applied poorly to the coating of monolithic mouldings. The reason for this is, in particular, the poor accessibility of the interior of a moulding. In order to produce coated mouldings having good chromatographic separation properties, the coating of the moulding must be homogeneous with respect to its thickness and its chemical composition over the entire moulding. Since the moulding is, in accordance with the invention, not filled completely with the organic polymer, the distribution of the coating in the interior of the moulding must, in order to prevent blockage of the pores of the moulding, be controlled as well as possible or a porogen which forms connecting pores must be added to the organic polymer.

Processes for the coating of particles frequently include the application of a polymer solution or a solution of monomer and free-radical initiator. The solvent is subsequently removed. This process cannot be applied in the coating of mouldings. During the drying of monolithic mouldings, the evaporation process of the solvent takes place over a relatively small surface (the outer surface of the monolith). The drying causes polymer solution to be constantly drawn out of the interior of the moulding (blotting paper effect; capillary action), which makes production of homogeneous coatings virtually impossible.

In accordance with the invention, coated mouldings are obtained which have improved properties, in particular improved stability, for example to alkaline solutions. Suitable coating processes for the production of coated mouldings which are improved in this way are those in which the coating solution is introduced into the moulding, and the chemi- or physisorption of the polymer coating takes place without the solvent of the coating solution being removed in advance. The solvent is only removed after completed chemi- or physisorption.

Suitable processes are, in particular, those in which polymerisation or polycondensation of monomers and/or oligomers can take place in the presence of the solvent or preferably processes in which prepolymers or monomers and/or oligomers can be precipitated from the solvent onto the moulding.

In both cases, it should furthermore be ensured that the coating of the moulding does not result in an excessively thick polymer coating on the outer wall of the moulding. Since the mouldings, for use in chromatography, generally have to be surrounded in a liquid-tight manner by a column cladding and have to be provided with connections for the feed and discharge of eluent, a thick and possibly irregular coating of the outer wall would make cladding considerably more difficult. In general, the coating of the outer wall would have to be removed first. This in turn may damage the outer wall of the moulding.

The coating of the mouldings is therefore preferably carried out, in accordance with the invention, already in a cladding which tightly surrounds at least the long side of the moulding. The cladding should be inert to the reagents and solvents involved in the coating. The coating solution can then preferably, in a similar manner to a chromatography column, be pumped into the clad moulding via suitable connections.

The coating can be carried out in exactly the same way by introducing an unclad moulding into an inert solvent for the coating. In the process, the moulding is firstly impregnated with the coating solution. It is subsequently dipped as completely as possible into an inert solvent in order to carry out the coating. Inert in this case means that the solvent is not involved in the polymerisation or polycondensation.

In order to carry out the process according to the invention, it may, if appropriate, be necessary chemically to modify the moulding before filling with the coating solution in order to provide the surface of the inorganic material with functional groups which are necessary for physi- or chemisorption of the organic polymer coating. Suitable processes are known to the person skilled in the art in the area of sorbents. Suitable reactions for the introduction of the functional groups are in principle those which are also used for the introduction of separation effectors into chromatographic support materials. For mouldings based on $SiO_2$, this is, in particular, the reaction with suitably functionalised silanes. The silanes can carry, for example, polymerisation-capable groups which facilitate covalent bonding to the moulding during the graft polymerisation of monomers and/or oligomers. Processes for the introduction of functionalities of this type are disclosed, for example, in WO 94/19687.

In just the same way, it may be advantageous, for homogeneous coating of the mouldings, to distribute a suitable free-radical initiator homogeneously on the surface of the moulding before impregnation of the moulding with the coating solution, in particular by covalent bonding to the moulding.

For the coating of the inorganic mouldings with the organic polymer, the moulding is firstly impregnated with a coating solution. This can be carried out, for example, by dipping the moulding into a corresponding solution or, in the case of a clad moulding, by pumping the coating solution through or on.

The coating of the moulding is then carried out depending on the nature of the coating solution. If the coating solution comprises prepolymers, these are precipitated onto the moulding under suitable conditions. If chemisorption of the prepolymers is the aim, this can be carried out, for example, by increasing the temperature, lowering the temperature, irradiation or addition of reagents which initiate the chemical reaction between moulding and prepolymer.

A process variant which has proven particularly advantageous for the production of a homogeneous coating is one in which the prepolymers are precipitated from the coating solution by reducing the solubility to below the solubility product, preferably by lowering the temperature. The considerable reduction in temperature results in the formation of a supersaturated solution, from which the prepolymers deposit uniformly on the moulding. In these process variants, the rate of precipitation can be controlled, for example, by the rate of temperature change.

In the case of prepolymers which are insoluble in the coating solution and are therefore applied as suspension, an increase in the temperature can also, where appropriate, effect uniform coating of the moulding, in particular if the polymers melt due to the temperature increase and consequently deposit on the surface of the moulding.

If the prepolymers are to be covalently bonded to the moulding, the bonding can be started after the precipitation through suitable initiation, such as irradiation, addition of reaction initiators, etc.

In addition, it is possible to apply a plurality of polymer layers, even different ones, successively to the moulding.

After completion of the coating, the moulding is rinsed thoroughly with suitable solvents in order to remove reaction residues, such as unreacted monomers or unadsorbed polymer.

The coated moulding is subsequently dried, preferably under reduced pressure.

The mouldings coated in accordance with the invention can be employed directly for chromatographic separations or first functionalised with separation effectors. These are, for example, ionic, hydrophobic, chelating or chiral groups. Processes for the introduction of functionalities of this type are known to the person skilled in the art in the area of chromatographic support materials and in relevant textbooks, for example Handbuch der HPLC [Handbook of HPLC], Ed. K. K. Unger; GIT-Verlag (1989) and Porous Silica, K. K. Unger, Elsevier Scientific Publishing Company (1979).

The mouldings according to the invention are particularly suitable for biochromatography since they are distinguished by good base stability on use of base-stable organic polymers and at the same time exhibit good separation efficiencies and a low column back pressure.

Furthermore, the mouldings coated in accordance with the invention can be employed as solid phase for the immobilisation of catalysts, for example biocatalysts, such as enzymes. Suitably functionalised mouldings can also serve as co-reactants for through-flow synthesis.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below and of the corresponding applications EP 02024250.9, filed on 31 Oct. 2002, and EP 02024251.7, filed on 31 Oct. 2002, are incorporated into this application by way of reference.

EXAMPLE

Example 1

Comparison of the Properties of a C18-functionalised moulding with a Polymer-coated Moulding According to the Invention 1.1 Production of Monoliths with Standard C18 Modification The usual method for masking a silica-gel surface in chromatography is surface modification with reaction with a hydrophobic silane.

For this purpose, 6 well-dried (100° C. under reduced pressure) porous monolithic silica mouldings (production corresponding to WO 98/29350; length 15 cm) which have a specific surface area of 300 $m^2$/g and a pore volume of 1 ml/g are placed in a reaction mixture of 100 ml of toluene and 15 ml of octadecyldimethylchlorosilane. In order to remove the air from the moulding, the reaction mixture is evacuated and re-aerated with nitrogen.

The reaction is carried out by heating for 24 hours at 110° C. After the reaction time, the mouldings are removed and freed from unreacted silane by extraction with toluene. After drying at 100° C. under reduced pressure, a weight increase of 20% is observed.

Measurement of the elemental analysis gives a content of 16.2% of carbon.

1.2 Production of Mouldings with a Polymer Coating of Styrene/Divinylbenzene

The coating of the silica-gel surface of the mouldings (same starting material as under 1.1) is carried out by polymerisation of a mixture of styrene and divinylbenzene. To this end, firstly a monomer mixture of 12 g of styrene and 6 g of divinylbenzene with 0.5 g of azoisobutyronitrile in 50 ml of toluene is prepared.

6 well-dried (100° C. under reduced pressure) silica mouldings having a length of 15 cm which have a specific surface area of 300 $m^2$/g and a pore volume of 1 ml/g are placed in the reaction mixture. In order to remove the air from the mouldings, the reaction mixture is evacuated and re-aerated with nitrogen.

For the polymerisation, the impregnated rods are then placed in a reaction apparatus containing fresh toluene preheated to 80° C. The reason for this is that only the coating solution is to be brought to reaction in the interior of the moulding in order that an external polymer layer on the moulding and/or solution polymer does not make cleaning more difficult and falsify the later stability investigation. After 5 hours at 80° C., the mouldings are removed and freed from unreacted monomer and unadsorbed polymer by extraction with toluene. After drying at 100° C. under reduced pressure, a weight increase of 6% is observed.

Measurement of the elemental analysis gives a content of 5.5% of carbon.

1.3 Reaction of a Clad Moulding Carrying a Polymerisable Functionalisation with Styrene/Divinylbenzene The coating of the silica-gel surface is carried out in this case by in-situ polymerisation of a mixture of styrene and divinylbenzene. In order to be able to covalently bond the polymer, the moulding was firstly reacted with a mixture of toluene and methacryloxypropyltrimethoxysilane.

A well-dried moulding having a length of 10 cm pre-clad with PEEK (production corresponding to WO 98/29350) which has a specific surface area of 300 $m^2$/g and a pore volume of 1 ml/g is conditioned at 80° C. in an HPLC oven. A mixture of 20 g of toluene and 2 g of methacryloxypropyltrimethoxysilane is pumped through the moulding at a flow rate of 0.5 ml/minute and subsequently rinsed with toluene.

A monomer mixture of 6 g of styrene and 3 g of divinylbenzene with 0.5 g of azoisobutyronitrile in 50 ml of toluene is subsequently prepared. The previously degassed reaction mixture is pumped through the moulding, which was conditioned at 80° C. in an HPLC oven, at a flow rate of 0.5 ml/minute. In order to remove unreacted monomer and unadsorbed polymer, the moulding is subsequently rinsed with 50 ml of toluene at 80° C. After drying at 100° C. under reduced pressure, a weight increase of 10% is observed.

Measurement of the elemental analysis gives a content of 9.3% of carbon.

1.4 Test for Stability of the Polymer Layer

A) Static Testing

In order to test the masking of the silica-gel surface and investigate for uniformity and impermeability of the polymer coating, the mouldings are subjected to sodium hydroxide solution treatment. Since silica gel has high solubility in sodium hydroxide solution, the surface coverage must reduce if the support material is attacked and dissolved.

For the testing, the mouldings are placed in 100 ml of a solution of 4 g of NaOH in 1 l of water (0.1N sodium hydroxide solution), and samples are withdrawn for investigation after 1 h, 5 h and 24 h. The samples are freed from soluble components and residual sodium hydroxide solution by intensive extraction with water. The mouldings are subsequently extracted firstly with methanol and then with toluene in order to remove polymer components no longer adsorbed.

The samples obtained are dried and investigated by elemental analysis. As comparison, the experiment was also carried out with a 1N sodium hydroxide solution.

B) Dynamic Testing

As an addition, a solution of 4 g of NaOH in 1 l of water (0.1N sodium hydroxide solution) is pumped through the PEEK-clad moulding for 24 hours at a flow rate of 0.2 ml/minutes, and the latter is washed by rinsing with water, methanol and toluene.

C) Result of the Testing

Table 1 shows the remaining carbon content of the mouldings or their condition after treatment with sodium hydroxide solution for various times:

FK1: C18-functionalised moulding (see 1.1)

FK2: moulding coated with styrene/divinylbenzene in toluene (see 1.2)

FK3: moulding coated with styrene/divinylbenzene in cladding (see 1.3)—only one value could be determined here since the moulding had to be broken out of the cladding for the determination of carbon content.

TABLE 1

| | FK1 | FK2 | FK3 |
|---|---|---|---|
| Starting value | 16.2% | 5.5% | 9.3% |
| 1 h (0.1N NaOH) | 10.5% | 5.5% | |
| 5 h (0.1N NaOH) | considerably dissolved | 5.4% | |
| 24 h (0.1N NaOH) | destroyed | 5.4% | 9.2% |
| 1 h (1N NaOH) | considerably dissolved | 5.4% | |
| 5 h (1N NaOH) | destroyed | 5.3% | |
| 24 h (1N NaOH) | destroyed | 5.3% | |

It was observed that a C-18-functionalised moulding loses a considerable amount of weight and thus also of carbon modification in sodium hydroxide solution and is in some cases destroyed or even completely dissolved. By contrast, the polymer-coated samples exhibit good stability to the sodium hydroxide solution. The experiment shows that the coating of an inorganic monolith with a polymer gives a material having novel, improved properties.

The stability test in alkaline solution enables the encapsulation of the mouldings by the polymer coating to be demonstrated. However, it is also entirely appropriate for some applications to use coatings with polymers which are unstable in sodium hydroxide solution.

For example, the production of biocompatible surface with hydrophilic polymers or with polysaccharides should also be considered here.

The example is also not restricted to the preparation of polymers on other inorganic supports.

1.5 BET Investigation

The FK2 in the coated moulding were characterised by measurement of the specific surface area and of the pore volume. A surface area of 280 $m^2/g$ and a pore volume of 0.92 ml/g were obtained here.

This result shows that the pores of the moulding were not "polymerised up", i.e. blocked, but instead a uniform layer has formed on the surface.

The pores of the moulding are thus not completely filled with polymer.

Accessible pore spaces thus remain in the monolith coated in accordance with the invention.

Example 2

Production of Coated Foreign Bodies by Precipitation of Prepolymers 2.1 Synthesis The following reactions were carried out in an apparatus according to FIG. 1. The moulding (1) is surrounded by a pressure-stable cladding (2). The coating solution, as well as further washing solutions, etc., are pre-mixed in container (3) and pumped by means of a pump (4) via a pressure reservoir (5) into a receiving container (6) made from pressure-resistant steel and from there through the moulding (1) into a waste container (7).

Firstly, the moulding (Chromolith®, Merck KGaA, Darmstadt, material $SiO_2$; internal diameter ID=4.6 mm; length L=25 mm) is conditioned with the solvent DMF used. The starting material is thus a moulding completely impregnated with solvent.

A coating solution comprising poly(methacrylate) solution (concentration c=10 $mgml^{-1}$) in dimethylformamide (DMF; p.a.) is prepared and introduced into the receiving container (6). Pressure is generated in the pressure reservoir (5), which is partly filled with air, by means of an HPLC pump (Bischoff brand), and the coating solution is thus forced into the moulding. Since air functions as pressure promoter (air cushion), it is ensured that the concentration of the polymer remains constant in this process. The pressure to be applied here is ~0.4 bar at a flow rate of 1 $mlmin^{-1}$.

The volume of the solution now present in the moulding is about V=0.33 ml. After 3 ml have flowed through, the moulding is removed, tightly sealed by means of screw connections and subsequently introduced into the prepared cold bath held at a temperature of −55° C. (methanol/dry ice) for 40 min. The solvent is then removed by means of a vacuum line at 40° C., 1 torr for 12 h.

In a similar manner, the coating can be carried out, for example, with poly(2-hydroxyethyl methacrylate) [P2HEMA], a copolymer of 2-hydroxyethyl methacrylate and ethyl methacrylate [P2HE.-E] or poly(octadecyl methacrylate) [POMA] instead of with poly(methacrylate) [PEMA].

A container with compressed gas, for example a nitrogen cylinder, can also be used for the pressure generation instead of an HPLC pump.

2.2 Carbon Content and Morphology

The carbon content of the coated mouldings, determined by elemental analysis, is shown in Table 2.

TABLE 2

| | P2HEMA | P2HE.-E | PEMA | POMA |
|---|---|---|---|---|
| % C | 0.97 | 1.78 | 2.14 | 1.05 |

Figure 2:
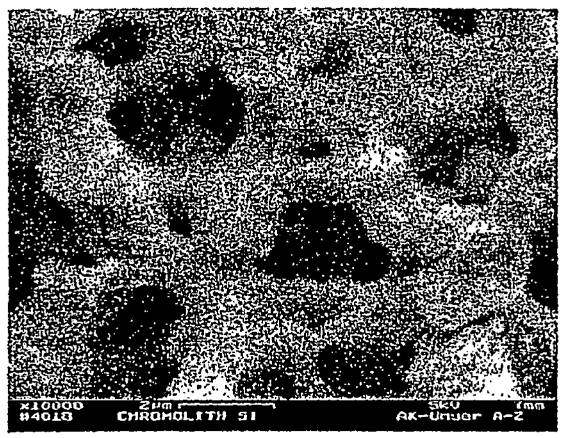
FIG. 2 shows in panel A an SEM photogragh of an uncoated moulding (Chromolith RTM from Merck KGaA) and in panel B a moulding coated with copolymer of 2-hydroxyethyl methacrylate and ethyl methacrylate.
Figure 2:
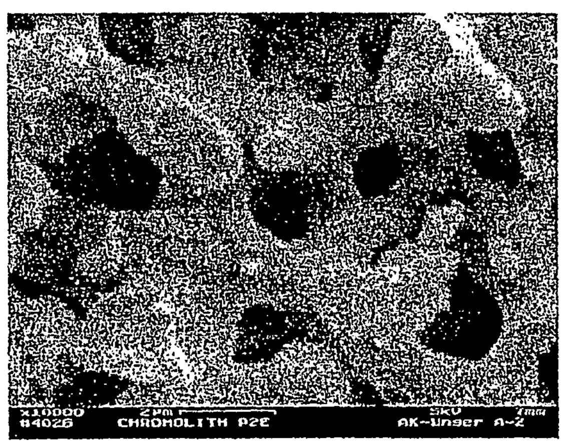

Scanning electron microscopy pictures (SEM) show that there is no difference between the coated and uncoated mouldings with respect to morphology. The macropore structure of the mouldings is retained. FIG. 2 shows the comparison of an SEM photograph of an uncoated moulding (Chromolith® from Merck KGaA) (FIG. 2A) and of a moulding coated with a copolymer of 2-hydroxyethyl methacrylate and ethyl methacrylate (FIG. 2B).

2.3 Chromatographic Behaviour

Before the chromatographic tests, the moulding now coated with poly(methacrylate) is conditioned for a further 1 h with the mobile phase at 1 $mlmin^{-1}$.

For the chromatographic investigations, three selected proteins: lysozyme, cytochrome C, myoglobin (LCM test mixture) were used as test mixture. The proteins were dissolved in water without addition of trifluoroacetic acid (TFA). The mobile phase used was an organic/aqueous eluent with addition of TFA in gradient mode:

Flow rate: 1 ml/min; detection: 215 nm, 400 nm;
Room temperature
Injection volume: 5 μl
From 95/5% (v/v) A/B in 5 min to 5/95% (v/v) A/B; with
A: water+0.1% TFA,
B: acetonitrile+0.09% TFA The counterpressure was about 20 bar for poly(methacrylate)-coated mouldings and about 30 bar for the uncoated moulding (Chromolith®).

The chromatograms obtained show that the elution profiles of the protein mixture change, as expected, depending on the hydrophobicity of the coating. The separation efficiency and the low column back pressure confirm the good suitability of the materials according to the invention as sorbent for chromatography.

Example 3

Production of Coated Foreign Bodies by Chemisorption

An azo derivative as initiator is covalently bonded to a monolithic moulding (Chromolith™ Si, Merck KGaA, Darmstadt, material $SiO_2$; internal diameter ID=4.6 mm; length L=25 mm) in an apparatus corresponding to Example 2.1, and monomers are subsequently polymerised on.

3.1. Coupling of p-(chloromethyl)phenyltrimethoxysilane to the Silica-Gel Surface A mixture of 3.95 g (16.04 mmol) of p-(chloromethyl) phenyltrimethoxysilane and 25 ml of dry tetrahydrofuran (THF; p.a.) is prepared. The monolith was conditioned with dry tetrahydrofuran (THF). The above mixture were then treated with nitrogen (dried over $H_2SO_4$) and introduced into the receiving container. Pressure was generated in the air-filled pressure reservoir by means of an HPLC pump (Bischoff brand), and the solution was thus forced into the monolith. The monolith was subsequently removed, tightly sealed by means of screw connections and allowed to stand vertically at room temperature for 35 h. The treated monolith was then washed with THF and subsequently with methanol.

The elemental analysis gave a carbon content % C: ~2.87%.

3.2. Coupling of 4,4'-Azobis(4-Cyanopentanoic Acid) (ACPA) to the Silane-derivatised Monolith The monolith derivatised with silane in accordance with 3.1 was conditioned with dry toluene. A solution of 3.63 g (10.66 mmol) of 4,4'-azobis(4-cyanopentanoic acid) (ACPA), 5.40 g of α-picoline and 15 ml of dry toluene was then treated with nitrogen (dried over $H_2SO_4$) and introduced into the receiving container. Pressure was generated in the air-filled pressure reservoir by means of an HPLC pump (Bischoff brand), and the solution was thus forced into the silane-derivatised monolith. The monolith was subsequently removed, tightly sealed by means of screw connections and placed vertically for 11 h in an oven at 50° C. in which the monolith had good heat contact. When the reaction is complete, the monolith is washed with toluene and subsequently with methanol.

The elemental analysis gave a carbon content % C:~4.64

3. Thermal Polymerisation with Ethyl Methacrylate

The monolith derivatised with azo initiator was conditioned with dry toluene. A solution of 1.86 g (15 mmol) of ethyl methacrylates (EMA), 0.30 g (1.5 mmol) of ethylene glycol dimethacrylate (EDMA) and 15 ml of dry toluene was then treated with nitrogen (dried over $H_2SO_4$) and introduced into the receiving container. Pressure was generated in the air-filled pressure reservoir by means of an HPLC pump (Bischoff brand), and the solution was thus forced into the monolith coupled with azo initiator. The monolith was subsequently removed, tightly sealed by means of screw connections and placed vertically for 4 h in an oven at 90° C. in which the monolith had good heat contact. When the reaction is complete, the monolith is washed with toluene and subsequently with methanol.

The elemental analysis gave a carbon content % C:~12.16

The carbon content of the product can be influenced by changing the concentrations of the reactants employed.

The invention claimed is:

1. A coated, clad moulding consisting essentially of a porous inorganic monolithic moulding having one side longer than the other(s) and having a cladding on the long side, wherein a free radical initiator is homogeneously distributed on the surface of said moulding before being coated with a polymer applied from a coating solution by impregnation, comprising at least one organic prepolymer or organic monomer and/or oligomer, which organic prepolymer or organic monomer and/or oligomer is precipitated from the coating solution by lowering the solution temperature and which polymer is physisorbed or chemisorbed on the inorganic moulding and bonded to said moulding via initiation, and wherein the polymer coating is stable against NaOH, and wherein all of the pores of the inorganic moulding have inner surfaces uniformly coated by said polymer such that a pore volume of the inorganic moulding is retained in the coated clad moulding.

2. A moulding according to claim 1, wherein the porous inorganic monolithic moulding consists of $SiO_2$.

3. A moulding according to claim 1, wherein the porous inorganic monolithic moulding has a bimodal pore structure with mesopores and macropores.

4. A moulding according to claim 3, wherein said mesopores have a diameter of between about 2 and 100 nm, and said macropores have a mean diameter of greater than 0.1 μm.

5. A moulding according to claim 1, wherein the organic polymer is polystyrene and/or polymethacrylate.

6. A moulding according to claim 1, wherein the organic polymer is physisorbed on the inorganic moulding.

7. A moulding according to claim 1, wherein said moulding is flat.

8. A moulding according to claim 7, wherein said moulding has a thickness of 0.2-20 μm.

9. A moulding according to claim 1, wherein said moulding is columnar and has a diameter of 0.1 cm-5 cm.

10. A moulding according to claim 9, wherein said moulding has a length of 1-30 cm.

11. A moulding according to claim 1, wherein said mouldings comprise an inorganic oxide.

12. A moulding according to claim 11, wherein said inorganic oxide is aluminium oxide, titanium dioxide or silicon dioxide.

13. A moulding according to claim 1, wherein said organic polymer is polystyrene, polymethacrylate, melamine, a polysaccharide, polysiloxane or a derivative or copolymer thereof.

14. A moulding according to claim 1, wherein said organic polymer is a copolymer of tetraalkoxysilane and methyltrialkoxysilane.

15. A moulding according to claim 1, wherein the carbon content of the coated moulding is from 0.97 to 1.05%.

16. A moulding according to claim 1, wherein said moulding is coated with poly(2-hydroxyethyl methacrylate) [P2HEMA], a copolymer of 2-hydroxyethyl methacrylate and ethyl methacrylate [P2HE-E], poly(octadecyl methacrylate) [POMA], or poly(methacrylate) [PEMA].

17. A moulding according to claim 1, wherein said organic polymer is forced thru said moulding under pressure and afterward the temperature is lowered.

18. A process for the production of a coated, clad porous inorganic monolithic moulding according to claim 1, comprising:

a) providing a porous inorganic monolithic moulding, b) impregnating the porous inorganic monolithic moulding from step a) with a coating solution comprising at least one organic prepolymer or organic monomer and/or oligomer, c) coating the moulding, whereby during the coating, the moulding is clad in an impermeable manner, at least on the long sides, with an inert material or stored in an inert solvent and d) washing and drying the moulding from step c) to remove reaction residues and solvent.

19. A process according to claim 18, wherein in step c) the prepolymer or monomer and/or oligomer is precipitated from the coating solution onto the inorganic moulding.

20. A process according to claim 19, wherein the precipitation is carried out by lowering the temperature.

21. A method for the chromatographic separation of at least two substances comprising introducing said substances to a moulding according to claim 1.

22. A method according to claim 21, wherein said chromotography is high pressure liquid chromatography and at least one of said substances is a biological material.

23. A method according to claim 21, wherein at least one of said substances is a protein or nucleic acid.

* * * * *